United States Patent [19]
Calverley

[11] Patent Number: 5,994,332
[45] Date of Patent: Nov. 30, 1999

[54] VITAMIN D ANALOGUES

[75] Inventor: Martin John Calverley, Herlev, Denmark

[73] Assignee: Leo Pharmaceutical Products Ltd. A/S, Ballerup, Denmark

[21] Appl. No.: 08/981,646

[22] PCT Filed: Dec. 2, 1996

[86] PCT No.: PCT/DK96/00502

§ 371 Date: Jan. 8, 1998

§ 102(e) Date: Jan. 8, 1998

[87] PCT Pub. No.: WO97/20811

PCT Pub. Date: Jun. 12, 1997

[30] Foreign Application Priority Data

Dec. 5, 1995 [GB] United Kingdom .................. 9524812

[51] Int. Cl.[6] .......................... A01N 45/00; C07C 401/00
[52] U.S. Cl. ............................................. 514/167; 552/653
[58] Field of Search ............................. 514/167; 552/653

[56] References Cited

PUBLICATIONS

Yoshida et al., Biological activity of Vit D derivatives, J. Pharmacobio–Dyn., 7(12), 962–8, 1984.
Masuda et al., In vitro metab. of the anti–psoriatic Vit. D analog, J. Biol. Chem., 269(7), 4794–803, 1994.
Makino et al., Secondary hyperparathyroidism Inhibitors, JP 07242550 A2, 1995.
Takahashi et al., 1,3–(OH)2 –cholestadiene derivatives, JP 02250865 A2, Oct. 8, 1990.
Schnoes et al., 1–hydroxy–25–keto–27–nor–cholecalciferol, WO 8002502, Nov. 1980.

Primary Examiner—Shelley A. Dodson
Assistant Examiner—Alton Pryor
Attorney, Agent, or Firm—Pillsbury Madison & Sutro LLP

[57] ABSTRACT

The present invention relates to compounds of formula (I) in which formula X is hydrogen or hydroxy; $R^1$ and $R^2$ stand for methyl or ethyl, or, when taken together with the carbon atom bearing the group X, can form a $C_3$–$C_5$ carbocyclic ring; Q is either a single bond or a $C_1$–$C_8$ hydrocarbylene in which one of any methylene groups not directly bonded to the carbonyl group may optionally be replaced by an oxygen atom (or methyl by hydroxy); Y is either a single bond or $C_1$–$C_8$ hydrocarbylene; and derivatives of (I) in which one or more of the hydroxy groups are masked as groups which can be reconverted to hydroxy groups in vivo. The compounds show anti-inflammatory and immunomodulating effects as well as strong activity in inducing differentiation and inhibiting undesirable proliferation of certain cells.

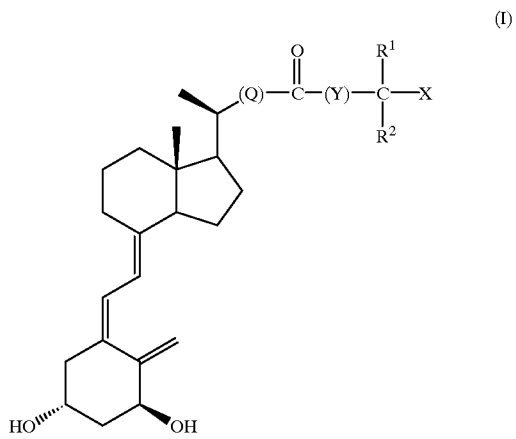

8 Claims, No Drawings

VITAMIN D ANALOGUES

This application is the national phase of international application PCT/DK96/00502 filed Dec. 2, 1996 which designated the U.S.

This invention relates to a hitherto unknown class of compounds which shows strong activity in inducing differentiation and inhibiting undesirable proliferation of certain cells, including skin cells and cancer cells, as well as immunomodulating and antiinflammatory effects, to pharmaceutical preparations containing these compounds, to dosage units of such preparations, and to their use in the treatment and/or prophylaxis of diseases characterized by abnormal cell differentiation and/or cell proliferation such as e.g. psoriasis and other disturbances of keratinization, HIV-associated dermatoses, wound healing, cancer, including skin cancer, and of diseases of, or imbalance in, the immune system, such as host versus graft and graft versus host reaction and transplant rejection, and autoimmune diseases, such as discoid and systemic lupus erythematosus, diabetes mellitus and chronic dermatoses of autoimmune type, e.g. scleroderma and pemphigus vulgaris, and inflammatory diseases, such as rheumatoid arthritis and asthma, as well as a number of other disease states including hyperparathyroidism, particularly secondary hyperparathyroidism associated with renal failure, cognitive impairment or senile dementia (Alzheimers disease) and other neurodegenerative diseases, hypertension, acne, alopecia, skin atrophy, e.g. steroid induced skin atrophy, skin ageing, including photo-ageing, and to their use for promoting osteogenesis and treating/preventing osteoporosis and osteomalacia.

The compounds of the invention constitute a novel class of vitamin D analogues represented by the general formula I:

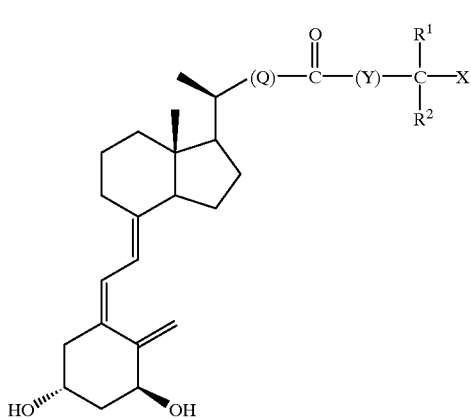

in which formula X is hydrogen or hydroxy; $R^1$ and $R^2$ stand for methyl or ethyl, or, when taken together with the carbon atom bearing the group X, can form a $C_3$–$C_5$ carbo-cyclic ring; Q is either a single bond or a $C_1$–$C_8$ hydrocarbylene in which one of any methylene groups not directly bonded to the carbonyl group may optionally be replaced by an oxygen atom (or methyl by hydroxy); Y is either a single bond or $C_1$–$C_8$ hydrocarbylene.

In the context of this invention, the expression hydrocarbylene indicates the diradical obtained after removal of 2 hydrogen atoms from a straight, branched or cyclic, saturated or unsaturated hydrocarbon.

Examples of Q and Y (when not a single bond) include, but are not limited to, methylene, ethylene, CH=CH, C≡C, trimethylene, CH=CHCH$_2$, CH$_2$CH=CH, C≡CCH$_2$, CH$_2$—C≡C, analogously derived $C_4$—(tetramethylene) and $C_5$-diradicals, and additionally, for Q: O—CH$_2$, O—CH$_2$CH$_2$, CH$_2$—O—CH$_2$CH$_2$, CH$_2$CH$_2$—O—CH$_2$, CH(OEt)—C=CH, CH(OH)—CH$_2$, CH(OEt)—C≡C, and for Y: phenylene (o-, m-, p-).

The compounds of the invention can comprise more than one diastereoisomeric form (e.g. E or Z configurations when a double bond is present in the group Q or Y; R and S configurations when a branching carbon is present). The invention covers all these diastereoisomers in pure form and also mixtures thereof. In addition, prodrugs of I in which one or more of the hydroxy groups are masked as groups which can be reconverted to hydroxy groups in vivo are also within the scope of the invention.

The compounds I may be obtained in crystalline form either directly by concentration from an organic solvent or by crystallisation or recrystallisation from an organic solvent or mixture of said solvent and a cosolvent which may be organic or inorganic, such as water. The crystals may be isolated in essentially solvent-free form or as a solvate, such as a hydrate. The invention covers all crystalline modifications and forms and also mixtures thereof.

A number of vitamin D analogues have recently been described that show some degree of selectivity in favour of the cell differentiation inducing/cell proliferation inhibiting activity in vitro as compared with the effects on calcium metabolism in vivo (as measured in increased serum calcium concentration and/or increased urinary calcium excretion), which adversely limit the dosage that can safely be administered. One of the first of these to appear, calcipotriol (INN) or calcipotriene (USAN), has been developed on the basis of this selectivity and is now recognized worldwide as an effective and safe drug for the topical treatment of psoriasis.

A study with another analogue (EB 1089) selected on this basis supports the concept that systemically administered vitamin D analogues may inhibit breast cancer cell proliferation in vivo at sub-toxic doses (Colston, K. W. et al., Biochem. Pharmacol. 44, 2273–2280 (1992)).

Promising immunosuppressive activities of vitamin D analogues have been reviewed (Binderup, L., Biochem. Pharmacol. 43, 1885–1892 (1992)). Thus, a series of 20-epivitamin D analogues has been identified as potent inhibitors of T-lymphocyte activation in vitro (Binderup, L. et al, Biochem. Pharmacol. 42, 1569–1575 (1991)). Two of these analogues, MC 1288 and KH 1060, systemically administered, have shown immunosuppressive activities in vivo in experimental animal models. Additive or synergistic effects were observed in combination with low-dose cyclosporin A. KH 1060, alone or in combination with cyclosporin A, has also been shown to prevent autoimmune destruction of transplanted islets in diabetic NOD mice (Bouillon, R. et al. In: Vitamin D, Proceedings of the Ninth Workshop on Vitamin D, Orlando, Fla., Walter de Gruyter, Berlin, 1994, pp 551–552). MC 1288 was able to prolong survival of cardiac and small bowel grafts in rats (Johnsson, C. et al. In: Vitamin D, Proceedings of the Ninth Workshop on Vitamin D, Orlando, Fla., Walter de Gruyter, Berlin, 1994, pp 549–550). However, in all these studies, the dosages of the analogues that produced significant immunosuppression also induced increases in serum calcium levels. There is therefore a continuing need for new analogues with high potency showing an acceptable combination of prolonged therapeutic activity and minimum toxic effects.

The present invention provides a hitherto undisclosed series of 20-epicholecalciferol analogues which are characterised by the presence of a keto function in the side chain. Analogues of vitamin D with a keto moiety (a carbonyl group bonded to two carbon atoms) in the side chain are not new: For example, Kureha Chemical Industries KK in Japanese Patent Application No. 210016/1983 disclose the use of 23-oxo-1,25,26-trihydroxycholecalciferol as an antitumour drug. Norman, A. W. and Mayer, E. of the University of California describe the synthesis of 1,25-dihydroxy-24-oxo-vitamin $D_3$ and 1,23,25-trihydroxy-24-oxo-vitamin $D_3$ (U.S. Pat. No. 4,495,181, 1985). The Teijin Company discloses 24-oxo-vitamin $D_3$ derivatives as neoplasm inhibitors in Japanese Patent Application No. 067,423/1985. Hamma, N. et al. describe fluorine derivatives of vitamin $D_3$ and process for producing the same (EP 250,755, 1988). McLane, J. A. et al. disclose stable and active metabolites of 1,25-dihydroxy-16-ene-cholecalciferol (U.S. Pat. No. 5,401,733, 1995). An example of a 22-oxa-24-ketone with cell differentiating activity is described by the Chugai Pharmaceutical Company in Japanese Patent Application No. 8,113,559/1996. However, it should be noted that these and other prior art side chain keto compounds that have been exemplified are characterised by the presence of the natural vitamin D configuration of the C-20 methyl group. Furthermore, these compounds contain the keto function located at either the second or the third atom away from C-20 (position 23 or position 24).

The compounds of the present invention differ from the prior art side chain keto compounds in the configuration of the C-20 methyl group; this has the β-projection as shown in the conventional representation used in formula I. In addition, the skeleton of the other C-20 substituent (the rest of the side chain) is not restricted to being either aliphatic or six-carbon, nor is the location of the keto group limited to either the second or the third atom away from C-20. These compounds have been discovered to possess exceptionally high immunosuppressive activities together with high tumor cell proliferation inhibiting activities. For example, the compound of Example 4 (Compound 104) was found to be more potent than the analogues MC 1288 and KH 1060 (the hitherto most potent compound tested) tablified in the above mentioned review (Binderup, 1992) in inhibiting allogeneic T-lymphocyte activation (mixed lymphocyte reaction) in vitro while it was less calcemic in vivo. Furthermore compound 104 was found to be at least ten times more potent than its corresponding 20-normal-configurated (20R) isomer in this immunological test system. The same orders of activity were observed in other in vitro immunological test systems such as the inhibition of the proliferative response of human lymphocytes induced by phytohemagglutinin (using the method described in Piekoszewski, W. et al., Immunopharmacology and Immunotoxicology, 16, 389–401 (1994)). The compounds of Examples 1 and 2 (Compounds 101 and 102) were also found to be over ten times more potent than their 20-isomers which had been synthesised for comparison purposes. The compounds were additionally highly active in the U937 cancer cell differentiation test, also referred to in the same review (Binderup, 1992), with the compounds of the present invention being approximately ten-fold more potent than their 20-isomers.

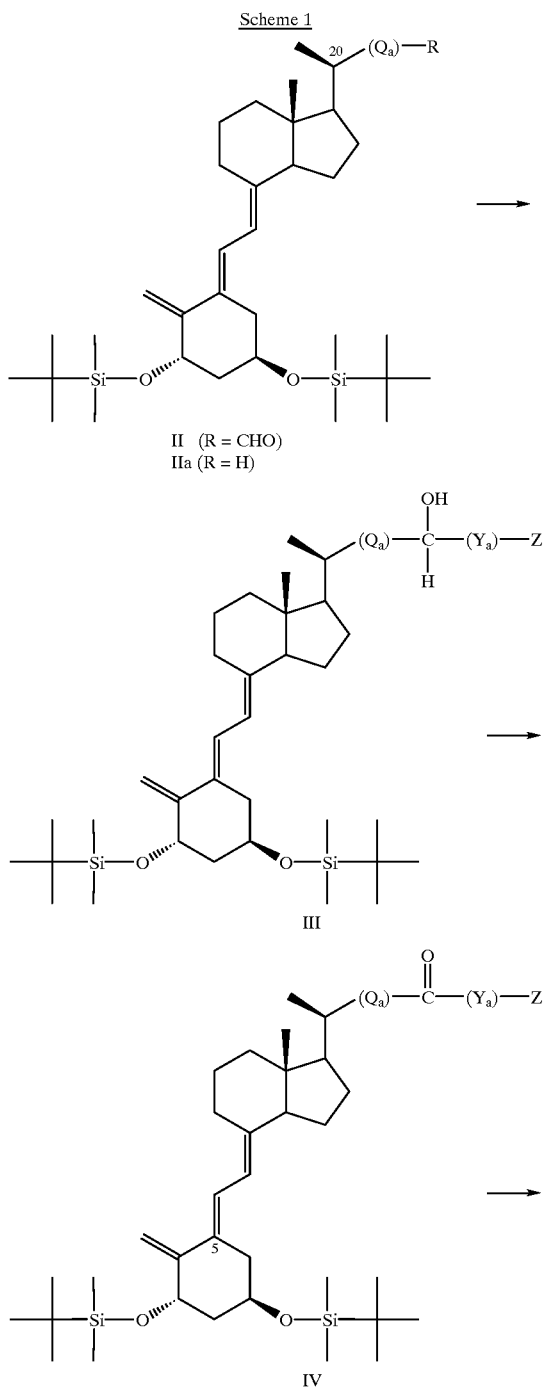

Scheme 1

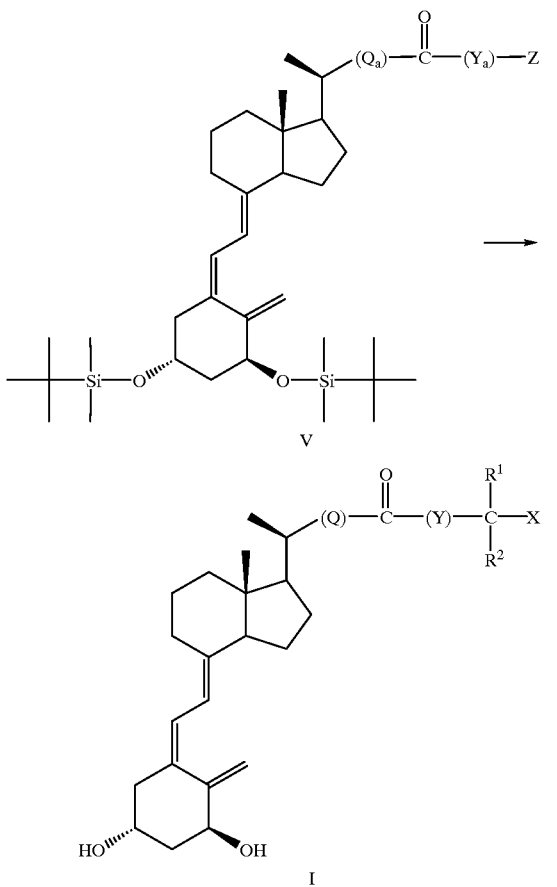

A compound of formula I may be prepared by the general method of Scheme 1. In this Scheme, the vitamin D nucleus building block aldehyde II, in which the aldehyde carbon is positioned appropriately to become the side chain keto carbon in the target compound I, is the starting material. This aldehyde II is either the simple compound in which $Q_a$ represents a single bond or a known derivative, or a new derivative prepared by a standard sequence of reactions. In the following, the symbol $Q_a$ in II indicates that this linking group may either be identical to Q in the compound I, or alternatively may be a group which can be converted to Q at any subsequent stage in the synthesis. Furthermore, the identity of $Q_a$ may change from intermediate to intermediate along the reaction sequence. However the actual identity will be apparent from the particular context.

Following the synthetic scheme as depicted:

1 II is reacted with an organometallic reagent of formula Z—($Y_a$)—M (wherein the metal radical M represents optionally Li or Mg-Hal; Hal=Cl, Br, or I), derived from a side chain building block of formula Z—($Y_a$)—H or Z—($Y_a$)—Hal, to establish the remainder of the carbon side chain skeleton in the intermediate III. The side chain alcohol configuration may be R or S or a mixture and is irrelevant to the synthesis. Again, the symbol $Y_a$ is used to indicate optional identity with or convertibility to Y (see above for analogous use of $Q_a$), and the symbol Z bears an analogous relationship to the group $C(R^1)(R^2)(X)$. In a complementary approach to the intermediate III, the metal radical (—M) replaces the aldehyde (—CHO) function in starting material II which is reacted with an aldehyde side chain building block of formula Z—($Y_a$)—CHO. The precursor IIa to the metallated derivative II (R=M) is prepared by a standard reaction sequence from an aldehyde of type II.

The remaining steps in the synthesis involve:
2 Oxidation of the alcohol to the ketone;
3 Optional conversion of the group $Q_a$ to Q;
4 Optional conversion of the group $Y_a$ to Y;
5 Optional conversion of the group Z to $C(R^1)(R^2)(X)$;
6 Triplet-sensitised photoisomerisation of the vitamin D triene (5E to 5Z); and
7 Removal of the vitamin D nucleus silyl protective groups;

The sequence of steps 1 through 7 may be altered (e.g. the photoisomerisation step (6) may precede the reaction (step 1) with the side chain building block), and several steps may be combined (e.g. the conditions of the desilylation step (7) may also effect a deprotection of the alcohol group X (step 5). Examples of conditions and reagents for the specified reactions (i.e. for steps 2, 6, and 7) are well known in the prior art of vitamin D analogue synthesis. Alternative routes to any one of the intermediates II through V or the compound I are available and will be obvious to the man skilled in the art.

The present compounds are intended for use in pharmaceutical compositions which are useful in the treatment of human and veterinary disorders as described above.

The amount required of a compound of formula I (hereinafter referred to as the active ingredient) for therapeutic effect will, of course, vary both with the particular compound, the route of administration and the mammal under treatment. The compounds of the invention can be administered by the parenteral, intra-articular, enteral or topical routes. They are well absorbed when given enterally and this is the preferred route of administration in the treatment of systemic disorders. In the treatment of dermatological disorders like psoriasis or eye diseases topical or enteral forms are preferred.

In the treatment of respiratory diseases like asthma an aerosol is preferred.

While it is possible for an active ingredient to be administered alone as the raw chemical, it is preferable to present it as a pharmaceutical formulation. Conveniently, the active ingredient comprises from 0.1 ppm to 0.1% by weight of the formulation.

By the term "dosage unit" is meant a unitary, i.e. a single dose which is capable of being administered to a patient, and which may be readily handled and packed, remaining as a physically and chemically stable unit dose comprising either the active material as such or a mixture of it with solid or liquid pharmaceutical diluents or carriers.

The formulations, both for veterinary and for human medical use, of the present invention comprise an active ingredient in association with a pharmaceutically acceptable carrier therefore and optionally other therapeutic ingredient (s). The carrier(s) must be "acceptable" in the sense of being compatible with the other ingredients of the formulations and not deleterious to the recipient thereof.

The formulations include e.g. those in a form suitable for oral, rectal, parenteral (including subcutaneous, intramuscular and intravenous), intra-articular and topical administration.

The formulations may conveniently be presented in dosage unit form and may be prepared by any of the methods well known in the art of pharmacy. All methods include the step of bringing the active ingredient into association with the carrier which constitutes one or more accessory ingredients. In general, the formulations are prepared by uniformly and intimately bringing the active ingredient into association with a liquid carrier or a finely divided solid carrier or both, and then, if necessary, shaping the product into the desired formulation.

Formulations of the present invention suitable for oral administration may be in the form of discrete units as capsules, sachets, tablets or lozenges, each containing a predetermined amount of the active ingredient; in the form of a powder or granules; in the form of a solution or a suspension in an aqueous liquid or non-aqueous liquid; or in the form of an oil-in-water emulsion or a water-in-oil emulsion. The active ingredient may also be administered in the form of a bolus, electuary or paste.

A tablet may be made by compressing or moulding the active ingredient optionally with one or more accessory ingredients. Compressed tablets may be prepared by compressing, in a suitable machine, the active ingredient in a free-flowing form such as a powder or granules, optionally mixed by a binder, lubricant, inert diluent, surface active or dispersing agent. Moulded tablets may be made by moulding, in a suitable machine, a mixture of the powdered active ingredient and suitable carrier moistened with an inert liquid diluent.

Formulations for rectal administration may be in the form of a suppository incorporating the active ingredient and a carrier such as cocoa butter, or in the form of an enema.

Formulations suitable for parenteral administration conveniently comprise a sterile oily or aqueous preparation of the active ingredient which is preferably isotonic with the blood of the recipient.

Formulations suitable for intra-articular administration may be in the form of a sterile aqueous preparation of the active ingredient which may be in microcrystalline form, for example, in the form of an aqueous microcrystalline suspension. Liposomal formulations or biodegradable polymer systems may also be used to present the active ingredient for both intra articular and ophthalmic administration.

Formulations suitable for topical administration, including eye treatment, include liquid or semi-liquid preparations such as liniments, lotions, gels, applicants, oil-in-water or water-in-oil emulsions such as creams, ointments or pastes; or solutions or suspensions such as drops.

For asthma treatment inhalation of powder, self-propelling or spray formulations, dispensed with a spray can, a nebulizer or an atomizer can be used. The formulations, when dispensed, preferably have a particle size in the range of 10 to 100 $\mu$.

Such formulations are most preferably in the form of a finely comminuted powder for pulmonary administration from a powder inhalation device or self-propelling powder-dispensing formulations. In the case of self-propelling solution and spray formulations, the effect may be achieved either by choice of a valve having the desired spray characteristics (i.e. being capable of producing a spray having the desired particle size) or by incorporating the active ingredient as a suspended powder in controlled particle size. These self-propelling formulations may be either powder-dispensing formulations or formulations dispensing the active ingredient as droplets of a solution or suspension.

Self-propelling powder-dispensing formulations preferably comprise dispersed particles of solid active ingredients, and a liquid propellant having a boiling point below 18° C. at atmospheric pressure. Generally, the propellant constitutes 45 to 99.9% w/w of the formulation whilst the active ingredient constitutes 0.1 ppm to 0.1% w/w, of the formulation.

In addition to the aforementioned ingredients, the formulations of this invention may include one or more additional ingredients such as diluents, buffers, flavouring agents, binders, surface active agents, thickeners, lubricants, preservatives, e.g. methyl hydroxy-benzoate (including antioxidants), emulsifying agents and the like. The compositions may further contain other therapeutically active compounds usually applied in the treatment of the above mentioned pathological conditions.

The present invention further concerns a method for treating patients suffering from one of the above pathological conditions, said method consisting of administering to a patient in need of treatment an effective amount of one or more compounds of formula I, alone or in combination with one or more other therapeutically active compounds usually applied in the treatment of said pathological conditions. The treatment with the present compounds and/or with further therapeutically active compounds may be simultaneous or with intervals.

In the treatment of systemic disorders daily doses of from 0.1–100 $\mu$g, preferably from 0.2–25 $\mu$g, of a compound of formula I are administered. In the topical treatment of dermatological disorders, ointments, creams or lotions containing from 0.1–500 $\mu$g/g, and preferably from 0.1–100 $\mu$g/g, of a compound of formula I are administered. For topical use in ophthalmology ointments, drops or gels containing from 0.1–500 $\mu$g/g, and preferably from 0.1–100 $\mu$g/g, of a compound of formula I are administered. The oral compositions are formulated, preferably as tablets, capsules, or drops, containing from 0.05–50 $\mu$g, preferably from 0.1–25 $\mu$g, of a compound of formula I, per dosage unit.

The invention is further illustrated by the following non-limiting Preparations and Examples:

PREPARATIONS AND EXAMPLES

The exemplified compounds I are listed in Table 1, whereas the starting materials and intermediates of general formulae II, III, IV and V are listed in Table 2.

The following standard abbreviations are used throughout this disclosure: Me=methyl; Et=ethyl; TBS=t-butyldimethylsilyl; THP=tetra-hydro-4H-pyran-2-yl; THF=tetrahydrofuran.

General

Ether refers to diethyl ether. Tetrahydrofuran (THF) was dried over sodium/benzophenone. Reactions were routinely run under an argon atmosphere unless otherwise noted. In the standard work-up procedure, the organic layer was separated, washed with saturated sodium chloride solution, dried over anhydrous magnesium sulphate, and concentrated in vacuo to give the product.

For $^1$H nuclear magnetic resonance spectra (300 MHz) chemical shift values ($\delta$) (in ppm) are quoted, unless otherwise specified, for deuteriochloroform solutions relative to internal tetramethylsilane ($\delta$=0.00) or chloroform ($\delta$=7.25). The value for a multiplet, either defined (doublet (d), triplet (t), quartet (q)) or not (m) at the approximate mid point is given unless a range is quoted (s=singlet, b=broad).

TABLE 1

Exemplified Compounds I (Details are provided for compounds where an Example Number is given; the other compounds may be prepared using analogous reaction sequences from the appropriate Compound II or IIa)

| Compound No. | Example No. | Q | Y | $R^1$ | $R^2$ | X |
|---|---|---|---|---|---|---|
| 101 | 1 | $(CH_2)_2$ | single bond | Me | Me | H |
| 102 | 2 | single bond | $(CH_2)_4$ | Me | Me | OH |
| 103 | 3 | single bond | $C\equiv C-CH_2$ | Et | Et | OH |
| 104 | 4 | $(CH_2)_2$ | single bond | Me | Me | OH |
| 105 | 5 | $(CH_2)_2$ | single bond | —$(CH_2)_4$— | | OH |
| 106 | 6 | *CH=CH | single bond | Me | Me | H |
| 107 |  | *CH=CH | single bond | Me | Me | OH |
| 108 | 7 | O—$(CH_2)_2$ | single bond | Et | Et | H |
| 109 | 8 | O—$(CH_2)_2$ | single bond | Et | Et | OH |
| 110 |  | $CH_2$—O—$(CH_2)_2$ | single bond | Me | Me | OH |
| 111 |  | *CH=CH | single bond | —$(CH_2)_2$— | | H |
| 112 |  | ¤CH(OEt)—C=CH* | single bond | Et | Et | OH |
| 113 |  | #CH(OH)—$CH_2$ | single bond | Me | Me | OH |
| 114 |  | ¤CH(OEt)—C≡C | single bond | Et | Et | OH |
| 115 |  | $CH_2$ | $(CH_2)_2$ | Me | Me | OH |
| 116 |  | $(CH_2)_3$ | single bond | Et | Et | OH |
| 117 |  | $CH_2$ | $CH_2$ | Me | Me | OH |

*E-Configuration of this double bond.
R-Configuration at this carbon.
¤S-Configuration at this carbon.

TABLE 2

Examples of intermediates of formula II through V (Scheme 1) (Details are provided for compounds where a Preparation Number is given; the other compounds may be prepared using analogous reaction sequences when not otherwise noted)

| Preparation Number | Compound Number | Compound Type | $(Q_a)$ | $(Y_a)$ | Z |
|---|---|---|---|---|---|
| * | 0001 | II | single bond | | |
| ** | 0002 | II | $(CH_2)_2$ | | |
| 01 | 0003 | III | single bond | $(CH_2)_4$ | $C(OSi(CH_3)_3)(Me)_2$ |
| 02 | 0004 | III | $(CH_2)_2$ | single bond | $CH(Me)_2$ |
| 03 | 0005 | III | single bond | $C\equiv C-CH_2$ | $C(O-THP)(Et)_2$ |
| 04 | 0006 | III | single bond | $(CH_2)_4$ | $C(OH)(Me)_2$ |
| 05 | 0007 | III | single bond | $C\equiv C-CH_2$ | $C(OH)(Et)_2$ |
| 06 | 0008 | IV | CH=CH*** | single bond | $CH(Me)_2$ |
| 07 | 0009 | IV | single bond | $(CH_2)_4$ | $C(OH)(Me)_2$ |
| 08 | 0010 | IV | single bond | $C\equiv C-CH_2$ | $C(OH)(Et)_2$ |
| 09 | 0011 | IV | $(CH_2)_2$ | single bond | $CH(Me)_2$ |
| 10 | 0011 | IV | $(CH_2)_2$ | single bond | $CH(Me)_2$ |
| 11a | 0012a | **** | | | |
| 11b | 0012 | IV | $(CH_2)_2$ | single bond | $C(OSi(CH_3)_3)(Me)_2$ |
| 12 | 0013 | V | $(CH_2)_2$ | single bond | $CH(Me)_2$ |
| 13 | 0014 | V | single bond | $(CH_2)_4$ | $C(OH)(Me)_2$ |
| 14 | 0015 | V | single bond | $C\equiv C-CH_2$ | $C(OH)(Et)_2$ |
| 15 | 0016 | V | $(CH_2)_2$ | single bond | $C(OSi(CH_3)_3)(Me)_2$ |
| 16a | 0017a | **** | | | |
| 16b | 0017 | II | O—$(CH_2)_2$ | | |
| 17 | 0018 | III | O—$(CH_2)_2$ | single bond | CH(Et)2 |
| 18 | 0019 | IV | O—$(CH_2)_2$ | single bond | $CH(Et)_2$ |
| 19a | 0020a | **** | | | |
| 19b | 0020 | IV | O—$(CH_2)_2$ | single bond | $C(OSi(CH_3)_3)(Et)_2$ |
| 20 | 0021 | V | O—$(CH_2)_2$ | single bond | $CH(Et)_2$ |
| 21 | 0022 | V | O—$(CH_2)_2$ | single bond | $C(OSi(CH_3)_3)(Et)_2$ |
|  | 0023 | II | $(CH_2)$—O—$(CH_2)_2$ | | |
| ** | 0024 | II | $CH_2$ | | |
| ** | 0025 | II | $(CH_2)_3$ | | |
| * | 0029 | IV | CH=CH*** | single bond | cyclopropyl |
| 22 | 0030 | IV | CH=CH*** | single bond | cyclopentyl |
|  | 0031 | IV | $(CH_2)_2$ | single bond | cyclopentyl |
|  | 0032 | IV | $(CH_2)_2$ | single bond | $C(OSi(CH_3)_3)(CH_2)_4$ |
| 23 | 0033 | V | CH=CH*** | single bond | $CH(Me)_2$ |
|  | 0034 | V | $(CH_2)_2$ | single bond | $C(OSi(CH_3)_3)(CH_2)_4$ |
| 24 | 0035 | II | CH(OEt)—CH=CH*** | | |
| 25 | 0036 | II | #CH(OTBS)—$CH_2$ | | |

TABLE 2-continued

Examples of intermediates of formula II through V (Scheme 1) (Details are provided for compounds where a Preparation Number is given; the other compounds may be prepared using analogous reaction sequences when not otherwise noted)

| Preparation Number | Compound Number | Compound Type | ($Q_a$) | ($Y_a$) | Z |
|---|---|---|---|---|---|
| 26 | 0037 | IIa | ¤CH(OEt)—C≡C | | |
| 27 | 0038 | III | ¤CH(OEt)—C≡C | single bond | CH(Et)$_2$ |

Footnotes to Table 2
Descriptions refer to Scheme 1, where applicable.
*Starting material (Compound 0001) or intermediate (Compound 0029), described in: Calverley, M.J., Tetrahedron, Vol. 43, pp. 4609–4619 (1987).
**Starting material, described in: Calverley, M.J. and Pedersen, H. Novel vitamin D analogues, International Patent Application WO 9,410,139-A1 (1994); Preparations 1, 2, and 3 (Compounds 0024, 0002, and 0025).
***E-Configuration of this double bond.
****Intermediate in which the structure of the side chain is not represented in Scheme 1. The full compound name is included in the Preparation.
R-Configuration at this carbon.
¤S-Configuration at this carbon.

General Procedure 1 (Preparations 01, 02, 17)

To a solution, maintained at about 5° C., of the Grignard reagent prepared from magnesium (3.3 mmol) and the Side chain building block (3 mmol) in dry THF (3 ml) was added via a syringe the Aldehyde (ca. 1 mmol) in dry THF (5 ml). After stirring at the same temperature for 30 min, the reaction mixture was partitioned between ether and saturated ammonium chloride solution. Standard work-up gave the oily Product.

Preparation 01: Compound 0003

(This preparation is a modification without separation of isomers of the synthesis described in Calverley, M. J. and Binderup, E. T. Novel vitamin D analogues. International Patent Application WO 9,100,271-A: (1991), Preparation 32:) Side chain building block: 6-bromo-2-methyl-2-(trimethylsilyloxy)hexane (0.80 g); Aldehyde: Compound 0001 (0.55 g, 0.96 mmol); Without further purification, the Product containing the Title Compound was used in the next step.

Preparation 02: Compound 0004

Side chain building block: 2-bromopropane (0.37 g); Aldehyde: Compound 0002 (0.60 g); Purification of the Product by chromatography on silica gel (50 g) (eluant: 15% ether in petroleum ether) gave the Title Compound. Oil; δ0.05 (12H, m), 0.54 (3H, s), 0.75 to 1.0 (9H, m), 0.85 (9H, s), 0.9 (9H, s), 1.05 to 2.1 (20H, m), 2.3 (1H, bd), 2.55 (1H, dd), 2.87 (1H, bd), 3.31 (1H, m), 4.21 (1H, m), 4.52 (1H, m), 4.93 (1H, m), 4.98 (1H, m), 5.81 (1H, d), 6.45 (1H, d).

Preparation 03: Compound 0005

(This preparation is a modification without separation of isomers of the synthesis described in Bretting, C. A. S. and Grue-Sørensen, G., International Patent Application WO 9,319,044-A1 (1993), Preparation 13:) To a solution, maintained at about −70° C., of the lithio-derivative prepared from n-butyl-lithium (1.6 M in hexanes; 3 mmol) and the side chain building block 4-ethyl-4-(tetrahydropyranyloxy)-hex-1-yne (0.65 g, 3.1 mmol) in dry THF (5 ml) was added via a syringe Compound 0001 (0.575 g, 1 mmol) in dry THF (2 ml). After stirring at the same temperature for 10 min and thereafter at 0° C. for 45 min, the reaction mixture was partitioned between ether and water. Standard work-up gave the oily Product. Purification by chromatography on silica gel (50 g) (eluant: 30% ether in petroleum ether) gave the Title Compound as an oil.

General Procedure 2 (Preparations 04, 05)

To a solution, maintained at about 25° C., of the Trimethylsilyl ether (0.96 mmol) or the THP ether (0.22 mmol) in THF (2 ml) was added pyridinium p-toluenesulphonate (0.010 g, 0.04 mmol, for trimethylsilyl ether; 0.150 g, 0.6 mmol, for THP ether) in ethanol (10 ml). After stirring at the same temperature for 15 min (trimethylsilyl ether) or 2 h (THP ether), the reaction mixture was partitioned between ethyl acetate and 5% sodium hydrogen carbonate solution. Standard work-up gave the oily Product.

Preparation 04: Compound 0006

Trimethylsilyl ether: Compound 0003, the crude product from Compound 0001, (0.96 mmol); Purification of the Product by chromatography on silica gel (50 g) (eluant: 40% ethyl acetate in petroleum ether) gave the Title Compound. Oil; δ0.06 (12H, m), 0.54 (3H, s), 0.83 (3H, d), 0.86 (9H, s), 0.89 (9H, s), 1.01 to 2.15 (24H, m), 1.2 (6H, s), 2.31 (1H, bd), 2.55 (1H, dd), 2.88 (1H, bd), 3.85 (1H, m), 4.21 (1H, m), 4.52 (1H, m), 4.93 (1H, m), 4.98 (1H, m), 5.83 (1H, d), 6.45 (1H, d).

Preparation 05: Compound 0007

THP ether: Compound 0005 (0.170 g, 0.217 mmol); Without further purification, the Product containing the Title Compound was used in the next step. δ0.05 (12H, m), 0.55 (3H, s), 0.85 (9H, s), 0.88 (6H, t), 0.89 (9H, s), 1.03 (3H, d), 1.15 to 2.1 (20H, m), 2.31 -(1H, bd), 2.37 (2H, m), 2.54 (1H, dd), 2.87 (1H, m), 4.21 (1H, m), 4.52 (1H, m), 4.61 (1H, m), 4.93 (1H, m), 4.98 (1H, m), 5.82 (1H, d), 6.44 (1H, d).

Preparation 06: Compound 0008

To a solution, maintained at about 25° C., of Compound 0001 (0.481 g, 0.84 mmol) in dry toluene (3 ml) was added the side chain building block 2-propylcarbonylmethylenetriphenylphosphorane (0.60 g, 1.72 mmol). After stirring at the same temperature for 10 min and thereafter at 110° C. for 5 h, the reaction mixture was partially concentrated in vacuo and diluted with ether. The solution was set aside to crystallise and filtered. The filtrate was concentrated in vacuo to give an oil. Purification by chromatography on silica gel (50 g) (eluant: 10% ether in petroleum ether) gave the Title Compound. Needles (from methanol); m.p. 123–124° C.; δ0.05 (12H, m), 0.5 (3H, s), 0.85 (9H, s), 0.89 (9H, s), 1 (3H, d), 1 to 1.82 (10H, m), 1.09 (6H, d), 1.95 (3H, m), 2.25 (1H, m), 2.3 (1H, bd), 2.54 (1H, dd), 2.81 (1H, m), 2.84 (1H, bd), 4.21 (1H, m), 4.52 (1H, m), 4.93 (1H, m), 4.97 (1H, m), 5.81 (1H, d), 6.1 (1H, d), 6.43 (1H, d), 6.77 (1H, dd).

Preparation 07: Compound 0009

To a solution, maintained at about 25° C., of Compound 0006 (0.69 g, 0.1 mmol) in dry dichloromethane (2 ml) was added solid pyridinium chlorochromate (0.04 g, 0.19 mmol). After stirring at the same temperature for 1 h, the reaction mixture was extracted with ether. The organic layer was separated and filtered and concentrated in vacuo to give an oil. Purification by chromatography on silica gel (15 g) (eluant: 20% ethyl acetate in petroleum ether) gave the Title Compound. Oil; δ0.06 (12H, m), 0.51 (3H, s), 0.85 (9H, s), 0.88 (9H, s), 1.02 (3H, d), 1.1 to 2.1 (20H, m), 1.2 (6H, s), 2.31 (1H, bd), 2.5 (4H, m), 2.85 (1H, m), 4.21 (1H, m), 4.51 (1H, m), 4.93 (1H, m), 4.97 (1H, m), 5.81 (1H, d), 6.43 (1H, d).

General Procedure 3 (Preparations 08. 09, 18)

To a solution, maintained at about 25° C., of the Alcohol (0.2 to 0.5 mmol) in dry dichloromethane (10 ml) was added portionwise 1,1,1-triacetoxy-l,1-dihydro-1,2-benziodoxol-3 (1H)-one (1.2 mol equiv.). After stirring at the same temperature for 15 min, the reaction mixture was partitioned between ether and 5% aqueous sodium bicarbonate solution also containing excess sodium thiosulphate. Standard work-up gave the oily Product.

Preparation 08: Compound 0010

Alcohol: Compound 0007, the crude product from Compound 0005, (0.217 mmol); The Product was purified by chromatography on silica gel (30 g) (eluant: 40% ether in petroleum ether) gave the Title Compound. Oil; δ0.05 (12H, m), 0.54 (3H, s), 0.85 (9H, s), 0.88 (9H, s), 0.92 (6H, t), 1.1 to 2.1 (14H, m), 1.14 (3H, d), 2.3 (1H, bd), 2.52 (2H, m), 2.56 (2H, s), 2.86 (1H, m), 4.21 (1H, m), 4.51 (1H, m), 4.93 (1H, m), 4.97 (1H, m), 5.81 (1H, d), 6.43 (1H, d).

Preparation 09: Compound 0011

Alcohol: Compound 0004 (0.322 g, 0.5 mmol); The Product was purified by chromatography on silica gel (30 g) (eluant: 5% ether in petroleum ether) gave the Title Compound. Needles (from methanol); m.p. 95–96° C.; δ0.05 (12H, m), 0.55 (3H, s), 0.83 (3H, d), 0.85 (9H, s), 0.89 (9H, s), 1.08 (6H, d), 1.2 to 2.1 (16H, m), 2.25 to 2.7 (5H, m), 2.86 (1H, bd), 4.21 (1H, m), 4.52 (1H, m), 4.93 (1H, m), 4.98 (1H, m), 5.81 (1H, d), 6.45 (1H, d).

Preparation 10: Compound 0011 (Alternative synthesis)

To a solution, maintained at about 25° C., of Compound 008 (1.15 g, 1.79 mmol) in toluene (50 ml) was added an aqueous solution of sodium dithionite (5.45 g, 31 mmol) containing sodium hydrogen carbonate (5.5 g) and methyltridecylammonium chloride (0.55 g). After vigorous stirring at the same temperature for 5 min and thereafter at 80° C. for 3 h, the reaction mixture was partitioned between ether and water. Standard work-up gave the oily Product. Purification by chromatography on silica gel (30 g) (eluant: 30% ether in petroleum ether) gave the Title Compound. Needles (from methanol); m.p. 95–96° C.; δ0.05 (12H, m), 0.55 (3H, s), 0.83 (3H, d), 0.85 (9H, s), 0.89 (9H, s), 1.08 (6H, d), 1.2 to 2.1 (16H, m), 2.25 to 2.7 (5H, m), 2.86 (1H, bd), 4.21 (1H, m), 4.52 (1H, m), 4.93 (1H, m), 4.98 (1H, m), 5.81 (1H, d), 6.45 (1H, d).

General Procedure 4 (Preparations 11a, 19a)

To a solution, maintained at about 5° C., of the Ketone (ca. 0.5 mmol) in dry dichloromethane (3 ml) was added hexamethyldisilazane (2 molar equiv.) and then iodotrimethylsilane (0.6 molar equiv.). After stirring at the same temperature for 1 h and thereafter at −20° C. overnight, the reaction mixture was partitioned between ether and 5% sodium hydrogen carbonate solution. Standard work-up gave the oily Product.

Preparation 11a: 24-Trimethylsilyloxy-1(S),3(R)-bis-(TES-oxy)-20(S)-9,10-seco-cholesta-5(E).7(E).10(19).24-tetraene (Compound 0012a)

Ketone: Compound 0011 (0.395 g, 0.61 mmol); Purification of the Product by chromatography on silica gel (30 g) (eluant: 1% ether in petroleum ether) gave the Title Compound. Needles (from methanol); m.p. 69–71° C.; δ0.05 (12H, m), 0.15 (9H, s), 0.53 (3H, s), 0.86 (3H, d), 0.86 (9H, s), 0.89 (9H, s), 1 to 2.08 (17H, m), 1.56 (3H, s), 1.59 (3H, s), 2.16 (1H, m), 2.3 (1H, bd), 2.55 (1H, dd), 2.86 (1H, bd), 4.21 (1H, m), 4.52 (1H, m), 4.93 (1H, m), 4.98 (1H, m), 5.81 (1H, d), 6.45 (1H, d).

General Procedure 5 (Preparations 11b 19b)

To a solution, maintained at about 5° C., of the Enol ether (ca. 0.2 mmol) in dry dichloromethane (5 ml) was added solid m-chloroperbenzoic acid (85%) (1.1 molar equiv.). After stirring at the same temperature for 15 min, the reaction mixture was partitioned between ether and 5% sodium hydrogen carbonate solution. Standard work-up gave the oily Product.

Preparation 11b: Compound 0012

Enol-ether: Compound 0012a (0.152 g, 0.21 mmol); Purification of the Product by chromatography on silica gel (15 g) (eluant: 5% ether in petroleum ether) gave the Title Compound. Needles (from methanol); m.p. 82–84° C.; δ0.05 (12H, m), 0.15 (9H, s), 0.55 (3H, s), 0.84 (3H, d), 0.85 (9H, s), 0.89 (9H, s), 1.15 to 2.08 (16H, m), 1.32 (6H, s), 2.3 (1H, bd), 2.56 (1H, dd), 2.62 (2H, m), 2.86 (1H, m), 4.21 (1H, m), 4.52 (1H, m), 4.93 (1H, m), 4.98 (1H, m), 5.81 (1H, d), 6.45 (1H, d).

General Procedure 6 (Preparations 12 through 15, 20. 21. 23)

To a solution of the 5E-Vitamin D compound (ca. 0.1 mmol), anthracene (9-acetylanthracene in Preparations 20 and 21) (0.03 g) and triethylamine (0.1 ml) in toluene or dichloromethane (5 ml) in a Pyrex flask was irradiated with light from a high pressure ultraviolet lamp, type TQ718Z2 (Hanau) at about 10° C. for 30 minutes. The reaction mixture was partially concentrated in vacuo to give the oily Product.

Preparation 12 : Compound 0013

SE-Vitamin D compound: Compound 0011 (0.067 g, 0.104 mmol) (in toluene); Purification of the Product by chromatogrmatography on silica gel (15 g) (eluant: 5% ether in petroleum ether) gave the Title Compound. Oil; δ0.05 (12H, m), 0.53 (3H, s), 0.82 (3H, d), 0.87 (18H, s), 1.05 to 2.05 (16H, m), 1.08 (6H, d), 2.2 (1H, dd), 2.3 to 2.67 (4H, m), 2.81 (1H, m), 4.18 (1H, m), 4.36 (1H, m), 4.85 (1H, m), 5.17 (1H, m), 6.00 (1H, d), 6.22 (1H, d).

Preparation 13: Compound 0014

5E-Vitamin D compound: Compound 0009 (0.080 g, 0.116 mmol) (in dichloromethane); Purification of the Product by chromatography on silica gel (15 g) (eluant: 30% ethyl acetate in petroleum ether) gave the Title Compound. Oil; δ0.05 (12H, m), 0.49 (3H, s), 0.87 (9H, s), 0.87 (9H, s), 1 (3H, d), 1.19 (3H, s), 1.19 (3H, s), 2.2 (1H, dd), 2.3 to 2.7 (4H, m), 2.81 (1H, m), 4.18 (1H, m), 4.36 (1H, m), 4.85 (1H, m), 5.17 (1H, m), 6 (1H, d), 6.22 (1H, d).

Preparation 14: Compound 0015

5E-Vitamin D compound: Compound 0010 (0.076 g, 0.109 mmol) (in dichloromethane); Purification of the Product by chromatography on silica gel (15 g) (eluant: 50% ether in petroleum ether) gave the Title Compound. Oil; δ0.05 (12H, m), 0.53 (3H, s), 0.87 (18H, s), 0.92 (6H, t), 1.14 (3H, d), 2.2 (1H, dd), 2.4 (1H, dd), 2.53 (1H, m), 2.57 (2H, s), 2.81 (1H, m), 4.18 (1H, m), 4.36 (1H, m), 4.85 (1H, m), 5.17 (1H, m), 6 (1H, d), 6.22 (1H, d).

Preparation 15: Compound 0016

5E-Vitamin D compound: Compound 0012 (0.062 g, 0.085 mmol) (in toluene); Purification of the Product by chromatography on silica gel (15 g) (eluant: 2 % ether in petroleum ether) gave the Title Compound. Oil; δ0.05 (12H, m), 0.15 (9H, s), 0.53 (3H, s), 0.84 (3H, d), 0.87 (18H, s), 1.32 (3H, s), 1.32 (3H, s), 2.2 (1H, dd), 2.4 (1H, m), 2.62 (2H, m), 2.81 ($1_H$, m), 4.18 (1H, m), 4.36 (1H, m), 4.85 (1H, m), 5.17 (1H, m), 6 (1H, d), 6.22 (1H, d).

Preparation 16a: (2–Cyanoethoxy-1(S) 3(R)-bis(TBS-oxy)-9,10-20(R) -seco-pregna-5 (E), -7(E),10(19),24-triene (Compound 0017a)

To a solution, maintained at about 25° C., of 20(R)-hydroxy-l(S),3(R)-bis-(TBS-oxy)-9,10-20(R)-seco-pregna-5(E),7(E),10(19),24-triene (1.3 g, 2.32 mmol) in dichloromethane (40 ml) was added a 40% aqueous solution of tetrabutylammonium hydroxide (20 ml, 15 mmol) followed by acrylonitrile (4.84 g, 91 mmol). After vigorous stirring at the same temperature overnight, the reaction mixture was partitioned between ether and water. Standard work-up gave the oily Product. Purification by chromatography on silica gel (80 g) (eluant: 20% ether in petroleum ether) gave the Title Compound; δ=0.05 (m, 12H), 0.56 (s, 3H), 0.86 (s, 9H), 0.88 (s, 9H), 1.10 (d, 3H), 1.10–2.20 (m, 13H), 2.30 (bd, 1H), 2.55 (dd, 1H), 2.56 (t, 2H), 2.87 (bd, 1H), 3.34 (m, 1H), 3.44 (m, 1H), 3.75 (m, 1H), 4.20 (m, 1H), 4.52 (dd, 1H), 4.92 (bt, 1H), 4.98 (bs, 1H), 5.79 (d, 1H), 6.45 (d, 1H).

Preparation 16b: Compound 0017

To a solution, maintained at about −70° C., of compound 0017a (0.9 g, 1.46 mmol) in dry ether (45 ml) was added via a syringe diisobutylaluminium hydride (1 M in hexanes; 2 mmol). After stirring at the same temperature for 1 h, the reaction mixture was partitioned between ether and saturated ammonium chloride solution. After standard work-up, the oily Product was purified by chromatography on silica gel (50 g) (eluant: 30% ether in petroleum ether) to give the Title Compound as an oil; δ=0.05 (m, 12H), 0.53 (s, 3H), 0.86 (s, 9H), 0.88 (s, 9H), 1.09 (d, 3H), 1.05–2.10 (m, 13H), 2.30 (bd, 1H), 2.54 (dd, 1H), 2.62 (dt, 2H), 2.86 (bd, 1H), 3.30 (m, 1H), 3.55 (m, 1H), 3.88 (m, 1H), 4.20 (m, 1H), 4.52 (dd, 1H), 4.93 (bt, 1H), 4.98 (bt, 1H), 5.79 (d, 1H), 6.44 (d, 1H), 9.78 (t, 1H).

Preparation 17: Compound 0018 (General Procedure 1)

Side chain building block: 3-bromopentane (0.45 g); Aldehyde: Compound 0017 (0.49 g, 0.8 mmol); Purification of the Product by chromatography on silica gel (50 g) (eluant: 20% ether in petroleum ether) gave the Title Compound as separate isomers which were recombined for use in the next step. First eluted isomer: Oil; δ=0.05 (m, 12H), 0.54 (s, 3H), 1.85 (m, 6H), 0.86 (s, 9H), 0.88 (s, 9H), 1.11 (d, 3H), 1.10–2.15 (m, 20H), 2.30 (bd, 1H), 2.54 (dd, 1H), 2.86 (bd, 1H), 3.18 (bs, 1H), 3.26 (m, 1H), 3.49 (m, 1H), 3.75 (m, 2H), 4.21 (m, 1H), 4.52 (dd, 1H), 4.93 (bt, 1H), 4.98 (bs, 1H), 5.79 (d, 1H), 6.45 (d, 1H); Second eluted isomer: Oil; δ=0.05 (m, 12H), 0.55 (s, 3H), 0.87 (m, 6H), 0.86 (s, 9H), 0.88 (s, 9H), 1.09 (d, 3H), 1.10–2.15 (m, 21H), 2.30 (bd, 1H), 2.54 (dd, 1H), 2.86 (bd, 1H), 3.29 (m, 1H), 3.44 (m, 1H), 3.72 (m, 2H), 4.21 (m, 1H), 4.52 (dd, 1H), 4.93 (bs, 1H), 4.98 (bs, 1H), 5.79 (d, 1H) , 6.45 (d, 1H)

Preparation 18: Compound 0019 (General Procedure 3)

Alcohol: Compound 0018 (0.22 g, 0.32 mmol); The Product was purified by chromatography on silica gel (30 g) (eluant: 10% ether in petroleum ether) gave the Title Compound; δ=0.05 (m, 12H), 0.54 (s, 3H), 0.83 (t, 3H), 0.84 (t, 3H), 0.86 (s, 9H), 0.89 (s, 9H), 1.07 (d, 3H), 1.05–1.80 (m, 16H), 1.85–2.07 (m, 3H), 2.25–2.35 (m, 2H), 2.55 (m, 1H), 2.86 (bd, 1H), 3.29 (m, 1H), 3.46 (m, 1H), 3.79 (m, 1H), 4.21 (m, 1H), 4.51 (dd, 1H), 4.93 (m, 1H), 4.97 (m, 1H), 5.79 (d, 1H), 6.45 (d, 1H).

Preparation 19a: (3-Trimethylsilyloxy-4-ethyl-hex-3-enyloxy)-1(S),3(R)-bis(TBS-oxy)-20(R) -9,10-seco-pregna-5(E) 7(E), -10(19)-triene (Compound 0020a) (General Procedure 4)

Ketone: Compound 0019 (0.178 g, 0.25 mmol); Purification of the Product by chromatography on silica gel (30 g) (eluant: 1% ether in petroleum ether) gave the Title Compound; δ=0.06 (m, 12H), 0.55 (s, 3H), 0.86 (s, 9H), 0.90 (s, 9H), 0.92 (t, 3H), 0.93 (t, 3H), 1.08 (d, 3H), 1.16 (s, 9H), 1.00–2.25 (m, 17H), 2.31 (bd, 1H), 2.37 (m, 2H), 2.55 (dd, 1H), 2.86 (bd, 1H), 3.31 (m, 2H), 3.63 (m, 1H), 4.21 (m, 1H), 4.53 (m, 1H) , 4.93 (m, 1H), 4.98 (m, 1H), 5.79 (d, 1H), 6.46 (d, 1H).

Preparation 19b: Compound 0020 (General Procedure 5)

Enol-ether: Compound 0012a (0.1 g, 0.13 mmol); Purification of the Product by chromatography on silica gel (15 g) (eluant: 5% ether in petroleum ether) gave the Title Compound; δ=0.06 (m, 12H),-0.17 (s, 9H), 0.55 (s, 3H), 0.77 (t, 3H), 0.78 (t, 3H), 0.86 (s, 9H), 0.89 (s, 9H), 1.08 (d, 3H), 1.00–2.15 (m, 17H), 2.29 (bd, 1H), 2.55 (dd, 1H), 2.70–2.92 (m, 3H), 3.30 (m, 1H), 4.45 (m, 1H), 3.78 (m, 1H), 4.21 (m, 1H), 4.53 (m, 1H), 4.93 (m, 1H), 4.98 (m, 1H), 5.79 (d, 1H), 6.45 (d, 1H).

Preparation 20: Compound 0021 (General Procedure 6)

5E-Vitamin D compound: Compound 0019 (0.06 g, 0.87 mmol) (in toluene); Without further purification, the Product containing the Title Compound was used in the next step. δ in agreement with structure.

Preparation 21: Compound 0022 (General Procedure 6)

5E-Vitamin D compound: Compound 0020 (0.07 g, 0.09 mmol) (in toluene); Without further purification, the Product containing the Title Compound was used in the next step. The following signals for the Title Compound could be discerned: δ=0.06 (m, 12H), 0.17 (s, 9H), 0.56 (s, 3H), 0.78 (t, 3H), 0.79 (t, 3H), 0.88 (s, 18H), 1.08 (d, 3H), 1.00–2.15 (m, 17H), 2.22 (dd, 1H), 2.45 (dd, 1H), 2.80 (m, 3H), 3.30 (m, 1H), 3.45 (m, 1H), 3.79 (m, 1H), 4.19 (m, 1H), 4.38 (m, 1H), 4.87 (m, 1H), 5.18 (m, 1H), 6.00 (d, 1H), 6.25 (d, 1H).

Preparations 22: Compound 0030

By replacing the side chain building block cyclopentylcarbonylmethylenetriphenylphosphorane for 2-propylcarbonylmethylenetriphenylphosphorane in Preparation 06, the Title compound was prepared.

Preparation 23: Compound 0033

5E-Vitamin D compound: Compound 0008 (0.09 g, 0.14 mmol) (in dichloromethane); Purification of the Product by chromatography on silica gel (15 g) (eluant: 30% ether in petroleum ether) gave the Title Compound; δ in agreement with structure.

Preparation 24: Compound 0035

The compound was prepared from Compound 0001 by the sequence: 1. $CH_2$=CH-MgBr; 2. separation of isomers by chromatography; 3. EtBr, KH; 4. $SO_2$; 5. 03; 6. $PPh_3$; 7. heat, $NaHCO_3$; 8. $Ph_3PCHCO_2Me$; 9. di-isobutylaluminium hydride; 10. 1,1,1-triacetoxy-1,1-dihydro-1,2-benziodoxol-3(1H)-one).

Preparation 25: Compound 0036

The compound was prepared from Compound 0001 by the sequence: 1. $CH_3CO_2Et$, $LiN(SiMe_3)_2$; 2. TBS-trifluoromethanesulphonate, 2,6-lutidine; 3. di-isobutylaluminium hydride.

Preparation 26: Compound 0037

The compound was prepared from Compound 0001 by the sequence: 1. Me$_3$SiC≡CH, n-butyl-lithium; 2. EtBr, KH; 3. tetrabutylammonium fluoride.

Preparation 27: Compound 0038

To a solution, maintained at about −70° C., of the lithio-derivative prepared from n-butyl-lithium (1.6 M in hexanes; 1 mmol) and Compound 0037 (1 mmol) in dry THF (5 ml) was added via a syringe 2-ethylbutanal (1 nmol) in dry THF (2 ml). After stirring at the same temperature for 10 min and thereafter at 0° C. for 45 min, the reaction mixture was partitioned between ether and water. Standard work-up gave the oily Product. Purification by chromatography on silica gel (50 g) (eluant: 30% ether in petroleum ether) gave the Title Compound as an oil.

General Procedure 7 (Examples)

To a mixture, maintained at about 25° C., of an ethyl acetate solution (about 0.3 ml) of the TBS-ether (ca. 0.1 mmol) in acetonitrile (5 ml) was added 48% aqueous hydrofluoric acid (0.5 g, 12 mmol). After stirring at the same temperature for 1 h, the reaction mixture was partitioned between ethyl acetate and 1N sodium hydroxide solution. After standard work-up gave the oily product was purified by chromatography on silica gel (15 g) (eluant: ethyl acetate) to give the Title Compound.

Example 1

24-Oxo-1(S).3(R)-dihydroxy-20(S)-9,10-seco-cholesta-5(Z),7(E),10(19) -triene (Compound 101)

TBS-ether: Compound 0013 (0.050 g, 0.078 mmol); Title Compound: Oil; δ0.56 (3H, s), 0.83 (3H, d), 1.09 (6H, d), 1.15 to 2.1 (18H, m), 2.31 (1H, dd), 2.4 (1H, ddd), 2.5 (1H, m), 2.59 (1H, dd), 2.61 (1H, m), 2.82 (1H, dd), 4.23 (1H, m), 4.43 (1H, m), 5 (1H, m), 5.32 (1H, m), 6.02 (1H, d), 6.37 (1H, d).

Example 2

1(S), 3(R) -Dihydroxy-20(R)-(6-hydroxy-6-methyl-1-heptanoyl) -9, 10-seco-pregna-5(Z) 7(E).10(19)-triene (Compound 102)

TBS-ether: Compound 0014 (0.065 g, 0.095 Mmol); Title Compound: Oil; δ0.52 (3H, s), 1.02 (3H, d), 1.1 to 2.05 (22H, m), 1.21 (6H, s), 2.3 (1H, s), 2.37 to 2.65 (4H, m), 2.81 (1H, m), 4.22 (1H, m), 4.42 (1H, m), 4.99 (1H, m), 5.33 (1H, m), 6.01 (1H, d), 6.35 (1H, d).

Example 3

1(S) 3(R)-Dihydroxy-20(R)-(5-hydroxy-5-ethyl-2-heptyn-1-oyl)-9,10-seco-pregna-5(Z) 7(E),10(19)-triene (Compound 103)

TBS-ether: Compound 0015 (0.07 g, 0.1 mmol); Title Compound: Oil; δ0.55 (3H, s), 0.93 (6H, t), 1.1 to 2.1 (20H, m), 1.14 (3H, d), 2.31 (1H, dd), 2.53 (1H, m), 2.57 (2H, s), 2.59 (1H, m), 2.82 (1H, dd), 4.23 (1H, m), 4.42 (1H, m), 4.99 (1H, m), 5.33 (1H, m), 6.01 (1H, d), 6.36 (1H, d).

Example 4

24-Oxo-1(S),3(R),25-Trihydroxy-20(S)-9,10-seco-cholesta-5(Z) 7(E) 10(19)-triene (Compound 104)

TBS-ether: Compound 0016 (0.053 g, 0.073 mmol); Title Compound: Oil; δ0.57 (3H, s), 0.85 (3H, d), 1.2 to 2.1 (18H, m), 1.39 (6H, s), 2.31 (1H, dd), 2.55 (3H, m), 2.83 (1H, m), 3.83 (1H, s), 4.23 (1H, m), 4.43 (1H, m), 5 (1H, m), 5.33 (1H, m), 6.02 (1H, d), 6.38 (1H, d).

Example 5

24-(1-Hydroxy-cyclopentyl)-24-oxo-1(S), 3(R)-dihydroxy-20(S)-9,10-seco-chola-5(Z),7(E),10(19)-triene (Compound 105)

TBS-ether: Compound 0034 (0.05 g, 0.066 mmol); Title Compound: Oil; δ0.57 (3H, s), 0.85 (3H, d), 1.2 to 2.1 (26H, m), 2.31 (1H, dd), 2.55 (3H, m), 2.83 (1H, m), 3.83 (1H, s), 4.23 (1H, m), 4.43 (1H, m), 5 (1H, m), 5.33 (1H, m), 6.02 (1H, d), 6.38 (1H, d).

Example 6

24-Oxo-1(S),3(R)-dihydroxy-20(R)-9,10-seco-cholesta-5(Z) 7(E),10(19),22(E)-tetraene (Compound 106)

TBS-ether: Compound 0033 (0.050 g, 0.078 mmol); Title Compound: Oil; δ0.56 (3H, s), 1 (3H, d), 1.09 (6H, d), 1.15 to 2.1 (16H, m), 2,25 (1H, m), 2.31 (1H, dd), 2.59 (1H, dd), 2.81 (1H, m), 2.82 (1H, dd), 4.23 (1H, m), 4.43 (1H, m), 5 (1H, m), 5.32 (1H, m), 6.02 (1H, d), 6.1 (1H, d), 6.37 (1H, d), 6.77 (1H, dd).

Example 7

1(S),3(R)-Dihydroxy-20(R)-(3-oxo-4-ethyl-1-hexyloxy)-9,10-seco-pregna-5(Z) 7(E),10(19)-triene (Compound 108)

TBS-ether: Compound 0021, the crude product from Preparation 20); Title Compound: Oil; δ0.55 (s, 3H), 0.84 (t, 3H), 0.85 (t, 3H), 1.08 (d, 3H), 1.10–1.80 (m, 15H), 1.90–2.07 (m, 4H), 2.25–2.35 (m, 2H), 2.60 (bd, 1H), 2.75 (bq, 2H), 2.82 (bd, 1H), 3.29 (m, 1H), 3.47 (m, 1H), 3.79 (m, 1H), 4.23 (m, 1H), 4.42 (m, 1H), 5.00 (bs, 1H), 5.33 (bs, 1H), 5.99 (d, 1H), 6.38 (d, 1H).

Example 8

1(S),3(R)-Dihydroxy-20(R)-(3-oxo-4-hydroxy-4-ethyl-1-hexyloxy)-9,10-seco-pregna-5(Z),7(E),10 (19)-triene (Compound 109)

TBS-ether: Compound 0022, the crude product from Preparation 21); Title Compound: Oil; δ0.54 (s, 3H), 0.77 (t, 3H), 0.79 (t, 3H), 1.07 (d, 3H), 1.05–2.10 (m, 19H), 2.30 (dd, 1H), 2.58 (m, 2H), 2.81 (m, 2H), 3.28 (m, 1H), 3.50 (m, 1H), 3.83 (s, 1H), 3.85 (m, 1H), 4.22 (m, 1H), 4.41 (m, 1H), 4.98 (m, 1H), 5.31 (m, 1H), 5.98 (d, 1H), 6.37 (d, 1H).

Example 7

Capsules Containing Compound 104

Compound 104 was dissolved in arachis oil to a final concentration of 1 μg/ml oil. Ten parts by weight of gelatine, 5 parts by weight of glycerin, 0.08 parts by weight potassium sorbate, and 14 parts by weight distilled water were mixed together with heating and formed into soft gelatine capsules. These were then filled each with 100 μl of the oily solution of Compound 104.

Example 8

Dermatological Cream Containing Compound 104

Compound 104 (0.05 mg) was dissolved in almond oil (1 g). To this solution was added mineral oil (40 g) and self-emulsifying beeswax (20 g). The mixture was heated to liquifidation. After the addition of hot water (40 ml), the mixture was mixed well. The resulting cream contains approximately 0.5 μg of compound 104 per gram of cream.

What we claim is:

1. A 20-epi compound of formula I

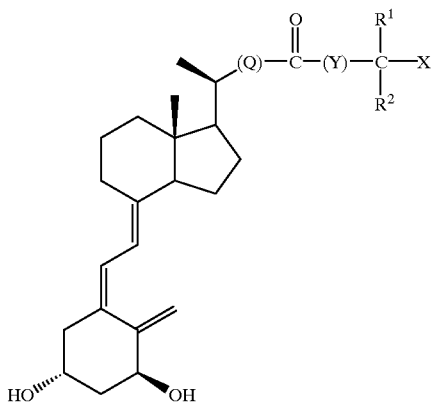

in which formula X is hydrogen or hydroxy; $R^1$ and $R^2$ stand for methyl or ethyl, or, when taken together with the carbon atom bearing the group X, can form a $C_3$–$C_5$ carbocyclic ring; Q is either a single bond or a $C_1$–$C_8$ hydrocarbylene in which one of any methylene groups not directly bonded to the carbonyl group may optionally be replaced by an oxygen atom; Y is either a single bond or $C_1$–$C_8$ hydrocarbylene.

2. A compound of formula I according to claim 1 in which X is hydroxy and Y is a single bond.

3. A diastereoisomer of a compound according to any one of claims 1 or 2, in pure form; or a mixture of such diastereoisomers.

4. A compound according to claim 2 which is 24-oxo-1(S), 3(R), 25-Trihydroxy-20(S)-9,10-seco-cholesta-5(Z), 7(E), 10(19)-triene.

5. A compound according to claim 2 which is 1(S), 3(R)-dihydroxy-20(R)-(3-oxo-4-hydroxy-4-ethyl-1-hexyloxy)-9,10-seco-pregna-5(Z), 7(E), 10(19)-triene.

6. A pharmaceutical composition containing an effective amount of one or more of the compounds of claim 1, together with pharmaceutically acceptable, non-toxic carriers and/or auxiliary agents.

7. A pharmaceutical composition according to claim 6 in dosage unit form containing from 0.1 ppm to 0.1% by weight of the dosage unit of a compound of formula I.

8. A method for the treatment of diseases characterized by at least one of abnormal cell differentiation and cell proliferation, diseases of, or imbalance in, the immune system, autoimmune diseases, inflammatory diseases, hyperparathyroidism, cognitive impairment or senile dementia, hypertension, acne, alopecia, skin atrophy, skin ageing, and promoting osteogenesis and treating osteoporosis and osteomalacia which comprises administering to a patient in need thereof an effective amount of a pharmaceutical composition according to claim 6.

* * * * *